United States Patent [19]
Colliver et al.

[11] Patent Number: 5,427,114
[45] Date of Patent: Jun. 27, 1995

[54] DUAL PRESSURE SENSING CATHETER

[75] Inventors: Michael D. Colliver, Belleville; Andrew C. Patania, Ann Arbor, both of Mich.

[73] Assignee: Fiberoptic Sensor Technologies, Inc., Ann Arbor, Mich.

[21] Appl. No.: 109,361

[22] Filed: Aug. 19, 1993

[51] Int. Cl.$^6$ .............................................. A61B 10/00
[52] U.S. Cl. ........................................................ 128/748
[58] Field of Search ................. 128/667, 675, 748, 774, 128/780; 73/705

[56] References Cited

U.S. PATENT DOCUMENTS

| | | | |
|---|---|---|---|
| 3,480,003 | 11/1969 | Crites | 128/748 |
| 3,565,056 | 2/1971 | Statham | 128/748 |
| 4,214,593 | 7/1980 | Imbruce et al. | 128/748 |
| 4,711,246 | 12/1987 | Alderson | 128/667 |
| 4,711,249 | 12/1987 | Brooks | 128/748 |
| 4,735,212 | 4/1988 | Cohen | 128/748 |
| 4,787,396 | 11/1988 | Pidorenko | 128/667 |
| 4,856,317 | 8/1989 | Pidorenko et al. | 73/705 |
| 4,901,731 | 2/1990 | Millar | 128/748 |
| 4,924,870 | 5/1990 | Wlodarczyk et al. | 128/667 |

OTHER PUBLICATIONS

Manfred Stöhrer, Urodynamics Handbook, F. M. WIEST GmbH+Co, Unterhaching W. Germany, pp. 3-27, 1989.

*Primary Examiner*—Max Hindenburg
*Attorney, Agent, or Firm*—Harness, Dickey & Pierce

[57] ABSTRACT

An apparatus for determining pressure at one or a number of intermediate points along a catheter inserted into a closed cavity. Fiberoptic cables extend from the proximal end of the catheter to the intermediate points at which pressure measurements are taken as well as to the distal tip of the catheter. The fiberoptic cables transport light signals injected at the proximal end and said light signals are illuminated in the direction of a flexible, reflective membrane. A pressure sensing coupler interconnects proximal and distal sections of the catheter sheath and also houses the pressure sensor. The pressure sensing coupler includes a plurality of radial ports which provide communication between the fluid in the cavity and a pressure sensing chamber, which is also in communication with the reflective membrane. The pressure sensing coupler also enables the passage of inner catheters through axial passageways for interconnection to other distally located pressure sensors.

19 Claims, 3 Drawing Sheets

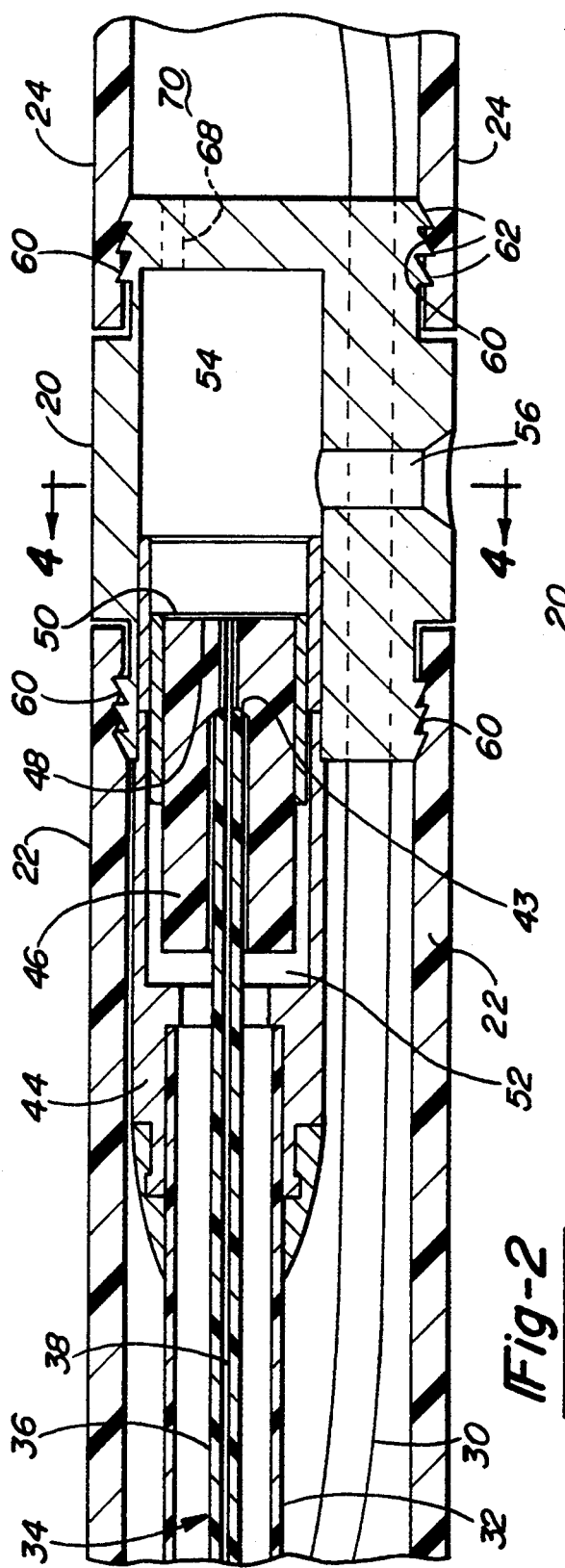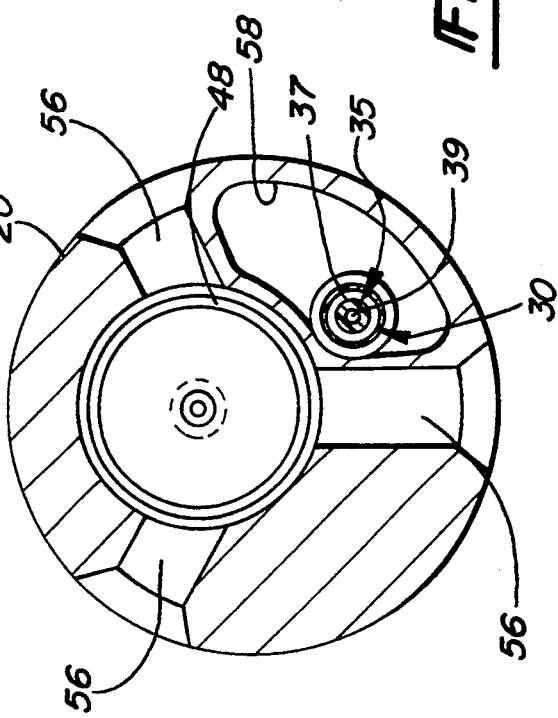

ial element. The Assignee
DUAL PRESSURE SENSING CATHETER

BACKGROUND OF THE INVENTION

This apparatus is related to a system for measuring pressure along any number of intermediate sites along a conduit such as a medical catheter inserted into a cavity. More particularly, the catheter may be used for simultaneous measurement of the pressure within a urinary bladder and the urethra leading to the bladder.

In a variety of situations involving the urodynamic clarification of the functional processes of the urinary tract and bladder, it is desirable to be able to measure the pressure differential between the urinary bladder and the urethra in order to determine the pressure profile of each particular anatomical element. The Assignee of the present application, Fiberoptic Sensor Technologies, Inc., (FST) has been in the forefront of the development of a variety of fiberoptic-based invasive pressure sensing devices and techniques. The advantages and uses of such devices and techniques are described in a number of U.S. patents previously issued to FST, including U.S. Pat. Nos. 4,711,246; 4,787,396; 4,856,317; and 4,924,870; and pending U.S. patent applications Ser. No. 07/748,082; filed on Aug. 21, 1991; Ser. No. 07/823,143, filed on Jan. 21, 1992; and Ser. No. 07/870,395, filed on Apr. 17, 1992, which are hereby incorporated by reference. The systems described in the above referenced documents generally employ a catheter having a deformable diaphragm positioned near the distal end of an optical fiber. Deflection of the diaphragm in response to external fluid pressure changes its shape and proximity to the end of the optical fiber. A light signal injected into the proximal end of the optical fiber exits the distal end of the fiber and is reflected by the deformable diaphragm to return along the fiber. The shape and spacing of the diaphragm from the fiber end affects the intensity of the returned light. The diaphragm is calibrated to provide a pressure measurement.

Fiber optic pressure sensors of the type described in FST's previously issued patents and pending applications possess a number of fundamental advantages over the previously used approach of fluid pressure measurement which comprises the use of a catheter lumen communicating with a remote site within the body which is connected to an external fluid column type pressure measuring device. These systems possess inherent disadvantages that arise from mechanically coupling a fluid pressure wave through a fluid column imbedded within a catheter to an external transducer. Both the mechanical compliance and the damping losses of the fluid column, the catheter material, and the transducer membrane result in broad resonance artifacts, typically occurring at frequencies in the vicinity of 10 to 20 Hertz and limit high frequency response. Moreover, any extensions of the catheter link used, for example, for a bedridden patient often result in impedance mismatching between tubing and connectors which can create additional resonance peaks. Because significant fluid pressure wave spectral components lie near the resonance frequencies of column sensors, some frequencies will be amplified relative to others, producing a distorted waveform. Waveform distortion is also produced by bubbles trapped in the fluid column. In addition, these types of pressure sensors suffer the disadvantage of distortions that are caused by patient or catheter movement. Motion produces a shift in fluid column position which adds baseline or low fluid frequency artifacts to the pressure waveform. It is for these reasons that direct pressure sensing at the position of the sensor within the catheter is becoming a preferred approach in clinical settings for pressure measurement and is gaining wider acceptance in such applications.

In addition to general fluid pressure monitoring, clinicians who specialize in the evaluation and diagnosis of urinary tract and bladder disorders are often interested in the differential pressure existing between the urinary bladder and the urethra. Such measurements yield a pressure profile which is particularly helpful in determining the closing capacity of specific urethral sections and may be especially important for the clarification of urinary incontinence. One commonly used method of measuring the pressure differential between the urinary bladder and the urethra generally includes the disposition of pressure sensor measurement means along the length of a catheter inserted into the urethra and the urinary bladder. The intermediate pressure sensing means generally comprises a balloon catheter which transmits pressure exerted within the urethra or the urinary bladder through the balloon to exert force on a pressure sensing measurement device. Such balloon catheters are not generally recommended for urethral pressure measurement because they cause spasms, yielding an inaccurate determination of urethral pressure measurements. Moreover, such balloon catheters generally operate on fluid column devices which include the inherent disadvantages as listed above as compared to fiberoptic measurement in determining fluid pressure.

SUMMARY OF THE INVENTION

This invention is directed at an apparatus for measuring pressures at one or a number of intermediate sites along a catheter inserted into a closed cavity. More particularly, this apparatus enables measurement of the fluid pressure within a urinary bladder simultaneously to the measurement of fluid pressure in the urethra. Multiple pressure measurements enable more accurate clarification of the functional processes of the urinary tract and bladder, yielding a more accurate pressure profile of the urinary system. Such an apparatus eliminates the need for insertion of balloon-type catheters into the urethra to obtain pressure measurements in addition to enabling pressure measurement to be taken at the distal end of the catheter.

The apparatus includes a catheter sheath comprised of a number of sections. A pressure sensing coupler interconnects the catheter sheath sections in order to form the multiple pressure sensing catheter. The pressure sensing couplers which interconnect the catheter sheath sections comprise fiberoptic sensors which measure the magnitude of light reflected from a deformable diaphragm whose shape changes in accordance with the pressure applied thereto. Deflection of the diaphragm varies the amount of light reflected back towards a photodetector. The amount of reflective light detected yields a pressure as a function of the light intensity. Opposite the deflectable diaphragm lies a pressure sensing chamber integral to the pressure sensing coupler which is in communication with the fluid whose pressure is to be sensed via a number of radial passageways into the pressure sensing chamber. The pressure sensing chamber has the added benefit of isolating the sensor element from any tissue surrounding the catheter. The radial passageways provide communication between the fluid whose pressure is to be sensed and the pressure sensing chamber, the pressure sensing chamber also being in communication with the deformable diaphragm.

Further objects, features and advantages of the invention will become apparent from a consideration of the following description and the appended claims when taken in connection with the accompanying drawings.

BRIEF DESCRIPTION OF THE DRAWINGS

FIG. 2 depicts an enlarged cross-sectional view of the fiberoptic, pressure sensing coupler shown by circle 2 of FIG. 1;

FIG. 4 depicts a typical cross-sectional view of the pressure sensing coupler along lines 4—4 of FIG. 2.

DETAILED DESCRIPTION OF THE INVENTION

Figure 1:
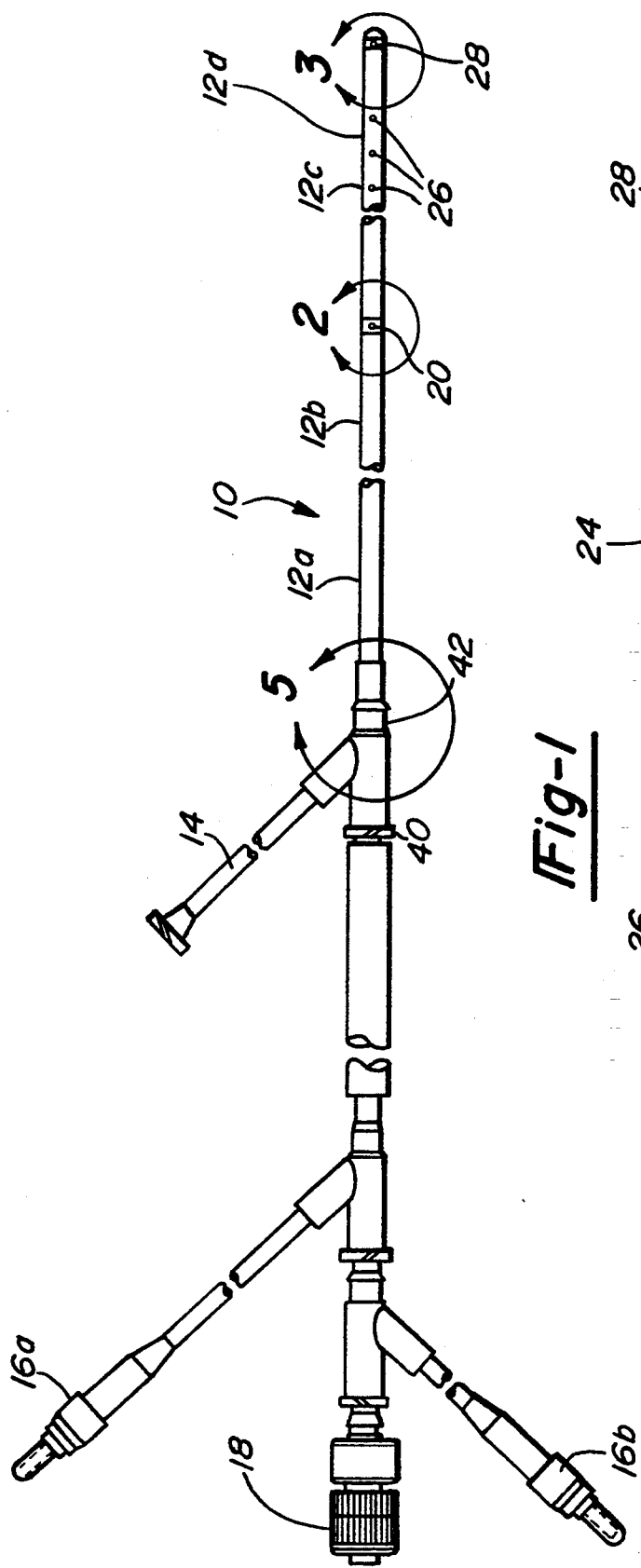
FIG. 1 depicts the multiple pressure sensing catheter according to an embodiment of the invention, including infusion ports located at the proximal end, an intermediate pressure sensor, and a pressure sensor located at the distal end.

Referring to FIGS. 1-2, a multiple pressure sensing catheter 10 according to this invention is shown. The multiple pressure sensing catheter 10 includes a number of outer catheter sections 12a-d, a fluid infusion port 14, optical connectors 16a-b, and vacuum calibration port 18. Outer catheter sections 12a-d are interconnected by one or a number of pressure sensing couplers 20, which function as a pressure sensor and a means of interconnecting, for example, outer catheter section 12b and outer catheter section 12c. Outer catheter sections 12a-d selectively include non-perforated sections and perforated sections having perforations 26 (catheter section 12d) which enable fluid infusion through fluid infusion port 14, to be described in further detail with respect to FIG. 5. At the distal tip of multiple pressure sensing catheter 10 is a distal pressure sensor 28, to be described in further detail with respect to FIG. 3. Fluid infusion port 14, when interconnected to a fluid source, enables fluid infusion into outer catheter sections 12a-d of multiple pressure sensing catheter 10, where said fluid exits through perforations 26, or optionally, fluid infusion into lumens within outer catheter sections 12a-d terminating at a predetermined position on pressure sensing catheter 10.

Referring to FIG. 2, an enlarged cross-sectional view of the area surrounding pressure sensing coupling 20, in accordance with circle 2 of FIG. 1 is shown. Pressure sensing coupler 20 interconnects outer catheter sections 12b and 12c. Two inner catheters 30, 32 are located internally to multiple pressure sensing catheter 10. Inner catheter 30 shown in elevation in FIG. 2 passes through a passageway within pressure sensing coupler 20 and continues distally within the multiple pressure sensing catheter 10. Inner catheter 32, shown in section in FIG. 2, connects to pressure sensing coupler 20 and provides a fiberoptic interface to enable the determination of fluid pressure surrounding pressure sensing coupler 20. Internal to inner catheter 32 is fiberoptic cable 34 comprising an buffer 36 and an inner cladding and core 38. Inner catheter 30 has a similar structure to that described with respect to inner catheter 34 in that it also contains a fiberoptic cable comprising a buffer 36 and an inner cladding and core 38. It should be noted that while inner catheters 30 and 32 have similar structures, inner catheter 32 is of a greater diameter than inner catheter 30.

Referring back to FIG. 1, the above described inner catheters, 30, 32 extend from their distal ends towards the proximal end of multiple pressure sensing catheter 10. Towards the proximal end of multiple pressure sensing catheter 10, a catheter adapter 40 is located proximally to the interconnection point 42 of fluid infusion port 14. The fiberoptic cable 34 comprising buffer 36 and cladding and core 38 extend proximally towards fiberoptic connectors 16a-b and vacuum calibration port 18. Inner catheter 30 also contains a fiberoptic cable 35, to be described with reference to FIG. 3, which is similarly terminated. Inner catheters 30, 32 terminate in the proximal direction at catheter adapter 40. In preferred embodiment, each of fiberoptic cables 34, 35 within inner catheters 30, 32, respectively, connect to one of optical connectors 16a or 16b. Optical connectors 16a-b enable the transmission and detection of light to and from fiberoptic cables 34 and 35, thereby enabling communication of light signals from one of the intermediate pressure sensing coupler 20 or the distal pressure sensor 28. Vacuum calibration port 18, when connected to a source of vacuum pressure, enables the application of vacuum pressure internally to inner catheters 30, 32. Such vacuum pressure is used for pressure sensor calibration at pressure sensing coupler 20 and distal pressure sensor 28, to be described in greater detail herein with respect to FIGS. 2 and 3. Vacuum pressure is transmitted distally to pressure sensing coupler 20 via axial passageways 58, to be described with respect to FIG. 4, which also enables passage of inner catheter 30, for example.

Referring to FIG. 2, inner catheter 32 connects to pressure sensor 44 which in turn connects to pressure sensing coupler 20. Buffer 36 of fiberoptic cable 34 extends into the body 46 of pressure sensor 44. Buffer 36 is then stripped away at location 43 and cladding and core 38 of fiberoptic cable 34 extends to the edge 48 of the body 46 of pressure sensor 44. Near the edge 48 of pressure sensor 44 is disposed a flexible reflective diaphragm 50 which moves inwardly and outwardly with respect to fiberoptic cladding and core 38 in response to varying pressure applied thereto, reflecting varying amounts of light. Pressure sensor 44 includes a chamber 52, enabling vacuum pressure communication between inner catheter 32 as exerted by a vacuum source (not shown) interconnected at vacuum calibration port 18. Such communication enables calibration of the fiberoptic sensors by applying a known vacuum incrementally and measuring the intensity of reflected light of reflective diaphragm 50.

Pressure exerted on flexible diaphragm 50 results from pressure sensing coupler 20 having a pressure sensing chamber 54 in communication with the surrounding body cavity through radial passageways 56. As shown in FIG. 4, pressure sensing coupler 20 includes a number of radial passageways 56 to enable communication between pressure sensing chamber 54 and the body cavity (not shown) surrounding pressure sensing coupler 20. Pressure sensing chamber 54 provides a significant advantage of isolating flexible membrane 50 from any tissue in the proximity of pressure sensing coupler 20, preventing the loading of flexible membrane 50. The significance of a number of radial passageways to enable the determination of pressure is that should one of the passageways 56 be occluded, fluid pressure detection can occur via one or both of the other passageways 56. Also included in pressure sensor coupler 20 at the distal interconnection point 60 is a small passage 68 for enabling a limited fluid drip into sensing chamber 54 from chamber 70. The limited fluid drip entering chamber 54 provides a self flooding feature to allow fluid communication between the chamber 54 and the surrounding body cavity. Fluid is provided into chamber 70 via an inner catheter tubing section distal to chamber 54. The self flooding feature provided by passageway 68 enables the benefit of pressure measurement in a body cavity when fluid supply from the body cavity is physiologically scarce. Note, however, that passageway 68 is sufficiently small so as to not adversely affect the accuracy of pressure measurements yielded by pressure sensor 44.

Also shown in FIG. 2 is inner catheter 30 passing through pressure sensing coupler 20. Passage of inner catheter 30 through pressure sensing coupler 20 occurs through one of a number of axial passageways 58 extending through pressure sensing coupler 20. Axial passageways 58 enable the passage of a plurality of additional catheters so that pressure sensing may occur at a number of additional intermediate locations along outer catheter sections 12a–d as well as at distal pressure sensing tip 28. Therefore, the number of pressure sensing locations along outer catheter sections 12a–d is determined primarily by the number of pressure sensing catheters that may transpose pressure sensing coupler 20 via axial passageways 58. Axial passageways 58 do not communicate with radial passageways 56 or with pressure sensing chamber 54. Thus, pressure sensing coupler 20 interconnects outer catheter section 12b and outer catheter section 12c and also provides uninterrupted passage of inner catheters 30, 32. Axial passageways 58 enable the passage of additional infusion or aspiration catheters proximally to pressure sensing coupler 20. Interconnection of catheter section 12b and catheter section 12c occurs by inserting an end of pressure sensing coupler 20 into the inner diameter of an outer catheter sections 12b–c. At interconnection points 60 of pressure sensing coupler 20, a barbed configuration 62 creates an interference condition between outer catheter section 12b–c and interconnection points 60 in order to ensure a sufficient fluid seal between the catheter section 12b–c and pressure sensing coupler 20. For an improved fixation, an adhesive may applied.

Figure 5:
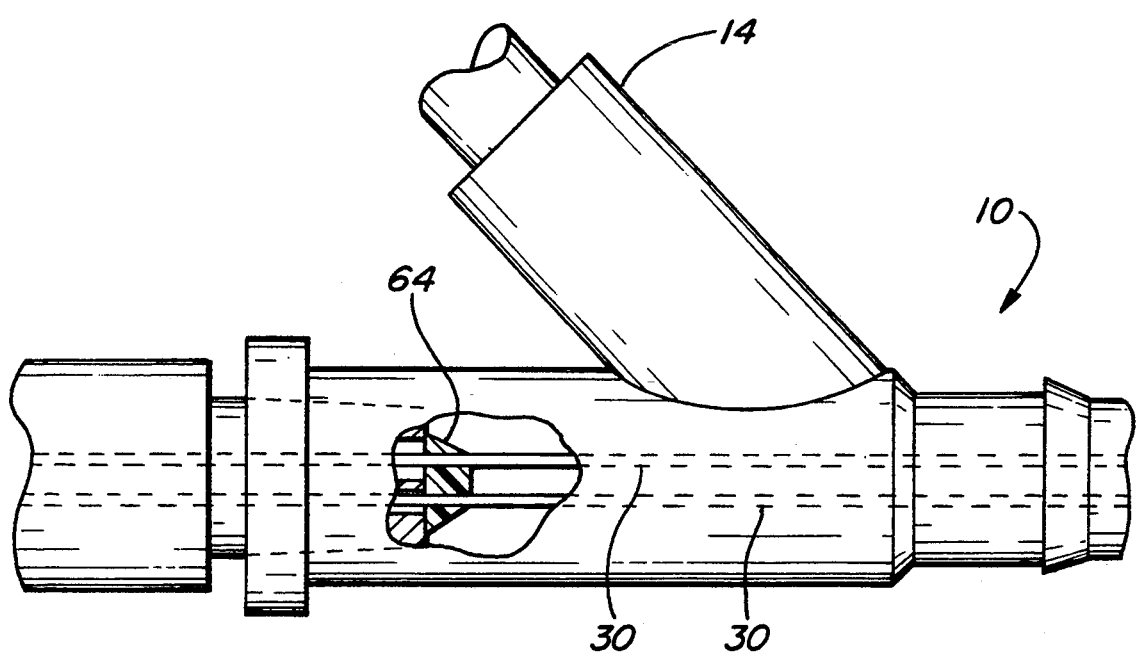
FIG. 5 depicts an enlarged cross-sectional view of an infusion port coupling as shown by circle 5 in FIG. 1.

FIG. 5 depicts an enlarged cross-sectional view of fluid infusion port 14 at its interconnection point 42 to multiple pressure sensing catheter 10. Inner catheters 30, 32 pass through multiple pressure sensing catheter 10 and through catheter plug 64, continuing on proximally in the direction of optical connectors 16a–b and vacuum calibration port 18. Catheter plug 64 creates a hermetic seal so that vacuum calibration may occur via vacuum calibration port 18. A hermetic seal also prevents fluid infused via fluid infusion port 14 from entering inner catheters 30, 32. Thus, infused fluid flows within outer catheter sections 12a–d external to inner catheters 30, 32 and exits through perforations 26. Because of the air-tight seal effectuated by catheter plug 64, such infused fluid does not interfere with the operation of the fiberoptic pathway.

Figure 3:
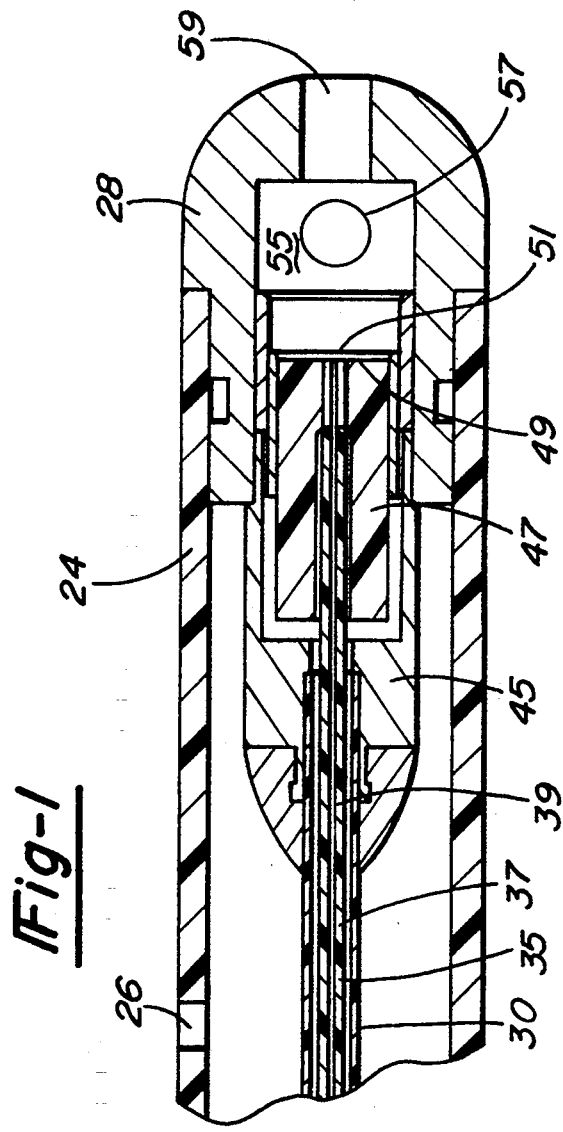
FIG. 3 depicts an enlarged cross-sectional view of the fiberoptic distal pressure sensing catheter tip as shown by circle 3 of FIG. 1.

FIG. 3 depicts an enlarged cross-sectional view of distal pressure sensor 28. This enlarged cross-section also depicts perforations 26 and outer catheter section 12d as it connects to distal pressure sensing tip 28. The operation of distal pressure sensor 28 is substantially the same as for intermediate pressure sensor 44 as described with respect to FIG. 2. Inner catheter 30 connects to pressure sensor 45, which is in turn connected to distal pressure sensing tip 28. The buffer 37 of fiberoptic cable 35 connects to the body 47 of pressure sensor 45, with the fiberoptic cladding and core 39 extending to the edge 49 of sensor body 47. Fiberoptic cladding and core 39 opposes flexible diaphragm 51 whose properties are as described with respect to FIG. 2. Diaphragm 51 communicates with pressure sensing chamber 55 which has at least one radial passage 57 and an axial passage 59, both of which communicate with the environment surrounding distal tip 28.

From the foregoing description of the multiple pressure sensing apparatus 10, it can be seen that fluid pressure measurements may be taken not only at distal tip 28, but also along a number of intermediate pressure sensing points (such points located in accordance with pressure sensing coupler 20) along outer catheter sections 12a–d. The number of intermediate points at which fluid pressure measurements may be obtained are in direct accordance with the number of pressure sensing couplers and accompanying inner catheters 30, disposed along the length of outer catheter sections 12a–d. This apparatus has particular use in the urodynamic evaluation of a urinary bladder and urethra. Such application of this apparatus enables the development of a differential pressure profile enabling the determination of a fluid pressure difference between the urinary bladder and the urethra.

It is to be understood that the invention is not limited to the exact construction illustrated and described above, but that various changes and modifications may be made without departing from the spirit and scope of the invention as defined in the following claims.

We claim:

1. A catheter for simultaneously measuring fluid pressure within a cavity at a plurality of sites along the catheter, comprising:
   a catheter sheath having a proximal and a distal end and formed of two or more sections;
   at least one coupler for interconnecting the catheter sections, the abutment of the catheter sections forming the catheter sheath from the proximal to the distal end; and
   first pressure sensing means integral to the coupler, in communication with the cavity and isolated in use from direct contact with any tissue surrounding the catheter, the pressure sensing means being responsive to pressure changes within the body cavity, enabling pressure sensing at locations intermediate to the proximal and distal end of the catheter.

2. The apparatus as defined by claim 1 wherein the catheter is a urodynamic device having a distal sensor placed in a urinary bladder and an intermediate sensor placed in a urethra.

3. The apparatus as defined by claim 1 further comprising a pressure sensing chamber integral to the coupler and in generally radial communication with the body cavity in which pressure is to be measured.

4. The apparatus as defined by claim 3 in which a plurality of radial passageways are integral to said coupler for establishing communication between the pressure sensing chamber and the body cavity, the passageways being displaced at varying angular positions.

5. The apparatus as defined in claim 1 further comprising a blind-ended bore integral to said coupler and functioning as a pressure chamber in generally radial communication with the body cavity and a sensor head positioned in an open end of said blind-ended bore.

6. The apparatus as defined by claim 5 further comprising optical fibers within the inner catheters for transmitting light pulses between the pressure sensing means and the proximal end of the single lumen catheter.

7. The apparatus as defined by claim 5 further comprising sealant means enabling vacuum calibration of the pressure sensing means via said pressure sensing lumen.

8. The apparatus as defined in claim 5 further comprising a passage in said coupler communicating between one of said catheter sections and said blind-ended bore for providing limited fluid flow from said catheter section to said blind-ended bore and the cavity, enabling self flooding pressure measurement in a body cavity with physiologically scarce fluid supply.

9. The apparatus as defined by claim 1 further comprising ridged interconnecting means located at a first axial end of said coupler and located at a second axial end opposite from said first axial end of said coupler.

10. The apparatus as defined in claim 1 further comprising passageways integral to said coupler and isolated from communication with the body cavity, the passageways enabling communication between catheter sections distal and proximal to the coupler.

11. The apparatus as defined by claim 1 further comprising fluid infusion means to infuse fluid into the catheter sheath substantially near the proximal end for exit at the distal end.

12. The apparatus as defined by claim 1 further comprising a plurality of catheter sheaths interconnecting each pressure sensing means to the proximal end of the single lumen catheter to provide communication therebetween.

13. The apparatus as defined in claim 1 further comprising a passage in said coupler communicating between one of the said catheter sections and the cavity adjacent said first pressure sensing means for providing limited fluid flow from said catheter section to said sensor and cavity adjacent thereto, enabling self flooding pressure measurement in a body cavity with physiologically scarce fluid supply.

14. An apparatus for simultaneously measuring pressure at a plurality of sites at remote locations within a body cavity, comprising:
a single lumen pressure sensing catheter having a proximal and a distal end and a plurality of sections;
at least one coupler for abutting the catheter sections, the abutment of the catheter sections forming a continuous catheter section from the proximal to the distal end where the coupler includes portals isolated from communication with the body cavity, the portals enabling communication between catheter sections distal and proximal to the coupler;
pressure sensing means integral to the coupler and in communication with the body cavity, the pressure sensing means being responsive to pressure changes within the body cavity, enabling pressure sensing at locations intermediate to the proximal and distal end of the catheter; and
a pressure sensing chamber integral to the coupler and in open communication with the body cavity in which pressure is to be measured;
secondary catheter means passing within the single lumen catheter for infusing fluid substantially near the proximal end for exit at the distal end;
a pressure sensing lumen operatively connecting the pressure sensing means and the proximal end of the single lumen catheter;
optical fibers within said pressure sensing lumen for transmitting light pulses between the pressure sensing means and the proximal end of the single lumen catheter; and
sealant means enabling vacuum calibration of the pressure sensing means via said pressure sensing lumen.

15. The apparatus as defined in claim 14 further comprising a passage in said coupler communicating between one of said catheter sections and said pressure sensing chamber adjacent said first pressure sensing means and further communicating with the cavity for providing limited fluid flow from said catheter section to said sensor and cavity adjacent thereto, enabling self flooding pressure measurement in a body cavity with physiologically scarce fluid supply.

16. An apparatus for simultaneously measuring pressure at a plurality of sites in a bodily channel comprising:
a flexible tubular body having multiple inlets distributed circumferentially therealong and a pressure sensing chamber provided in said body, said inlets providing communication between said pressure sensing chamber integral to said body and the site in which pressure is to be measured, wherein said pressure sensing chamber is disposed from an exterior surface of said tubular body.

17. The apparatus as defined in claim 16 further comprising a catheter section carried in the apparatus; a passage provided in the apparatus communicating between said catheter and said pressure sensing chamber and further communicating with the cavity for providing limited fluid flow from said catheter section to said sensor and cavity adjacent thereto, enabling self flooding pressure measurement in a body cavity with physiologically scarce fluid supply.

18. In a catheter for measuring pressure within a cavity at a site along the catheter, a catheter sheath including at least one catheter section providing a flexible tubular body having a proximal and a distal end; pressure sensing means carried in the catheter adjacent the sheath which provides a pressure sensing chamber integral to the pressure sensing means and communicating with the cavity in which pressure is to be measured, the improvement comprising:
a passage provided in the catheter in fluid communication with the pressure sensing chamber and a fluid chamber in the catheter for providing limited fluid flow from said fluid chamber to the sensor and cavity adjacent thereto, enabling self flooding pressure measurement in a body cavity with physiologically scarce fluid supply.

19. The apparatus as defined in claim 18 wherein the catheter has a plurality of pressure sensing means integral therewith and a plurality of fluid chambers in the catheter wherein at least one of the pressure sensing means having a pressure chamber opening to the cavity communicates through at least one of the said passages with at least one of the said fluid chambers for providing limited fluid flow, enabling self flooding pressure measurement positionally within at least one location of a body cavity having physiologically scarce fluid supply.

* * * * *